US010966655B2

(12) United States Patent
Chen

(10) Patent No.: US 10,966,655 B2
(45) Date of Patent: Apr. 6, 2021

(54) TISSUE HYDRATION MONITOR

(71) Applicant: Hydrostasis, Inc., San Diego, CA (US)

(72) Inventor: Debbie K. Chen, San Diego, CA (US)

(73) Assignee: HYROSTASIS, INC., San Diego, CA (US)

( * ) Notice: Subject to any disclaimer, the term of this patent is extended or adjusted under 35 U.S.C. 154(b) by 0 days.

(21) Appl. No.: 16/395,148

(22) Filed: Apr. 25, 2019

(65) Prior Publication Data
US 2019/0328323 A1  Oct. 31, 2019

Related U.S. Application Data

(60) Provisional application No. 62/663,926, filed on Apr. 27, 2018.

(51) Int. Cl.
*A61B 5/00* (2006.01)

(52) U.S. Cl.
CPC .......... *A61B 5/4875* (2013.01); *A61B 5/0075* (2013.01); *A61B 5/443* (2013.01); *A61B 5/6831* (2013.01); *A61B 5/6833* (2013.01); *A61B 5/746* (2013.01); *A61B 5/4261* (2013.01); *A61B 5/6813* (2013.01); *A61B 5/7267* (2013.01); *A61B 5/7278* (2013.01)

(58) Field of Classification Search
CPC ... A61B 5/4875; A61B 5/0075; A61B 5/4261; A61B 5/443; A61B 5/6813; A61B 5/6831; A61B 5/6833; A61B 5/7267; A61B 5/7278; A61B 5/746
USPC .......................................... 340/870.01, 870.1
See application file for complete search history.

(56) References Cited

U.S. PATENT DOCUMENTS

| 4,243,883 | A  | 1/1981 | Schwartzmann |
| 6,172,743 | B1 | 1/2001 | Kley et al. |
| 6,442,407 | B1 | 8/2002 | Wenzel et al. |
| 6,591,122 | B2 | 7/2003 | Schmitt |
| 6,675,029 | B2 | 1/2004 | Monfre et al. |
| 6,898,451 | B2 | 5/2005 | Wuori |
| 7,236,811 | B2 | 6/2007 | Schmitt |
| 7,239,902 | B2 | 7/2007 | Schmitt et al. |

(Continued)

FOREIGN PATENT DOCUMENTS

| WO | 2014127127 A9 | 8/2014 |
| WO | WO 2018044959 | * 3/2018 |

OTHER PUBLICATIONS

Acoustical Physics; vol. 62 issue 4; Published Jul. 2016; Acoustical Method of Whole-Body Hydration Status Monitoring.*

(Continued)

*Primary Examiner* — Hirdepal Singh
(74) *Attorney, Agent, or Firm* — Eleanor Musick; Musick Davison LLP

(57) ABSTRACT

A tissue hydration monitor and method includes a sensor module having a plurality of LEDs positioned to emit a plurality of different wavelengths of light toward the user's skin and a detector that detects light transmitted and reflected through the user's skin to generate signals corresponding to an intensity of detected light at each of the different wavelengths. A processor/controller module generates a baseline hydration level based on the received signals, calculates a relative hydration level, and generates an output indicative of relative hydration personalized to the user. The housing is secured against the user's skin by an adhesive patch or a strap.

21 Claims, 8 Drawing Sheets

(56) References Cited

U.S. PATENT DOCUMENTS

| | | |
|---|---|---|
| 7,657,292 B2 | 2/2010 | Baker, Jr. et al. |
| 7,713,196 B2 | 5/2010 | Baker, Jr. et al. |
| 8,181,410 B2 | 5/2012 | Debreczeny et al. |
| 8,457,722 B2 | 6/2013 | Schmitt et al. |
| 8,509,866 B2 | 8/2013 | Schmitt et al. |
| 9,078,619 B2 | 7/2015 | Panasyuk et al. |
| 9,351,671 B2 | 5/2016 | Ruchti et al. |
| 9,585,604 B2 | 3/2017 | Ruchti et al. |
| 9,766,126 B2 | 9/2017 | Gulati et al. |
| 9,833,180 B2 | 12/2017 | Shakespeare et al. |
| 10,420,491 B2 * | 9/2019 | Rajan .............. A61B 5/02007 |
| 2002/0084417 A1 | 7/2002 | Khalil et al. |
| 2006/0253016 A1 | 11/2006 | Baker, Jr. et al. |
| 2007/0085995 A1 | 4/2007 | Pesach et al. |
| 2007/0118027 A1 | 5/2007 | Baker, Jr. et al. |
| 2007/0273504 A1 | 11/2007 | Tran |
| 2008/0221411 A1 | 9/2008 | Hausmann et al. |
| 2012/0088982 A1 * | 4/2012 | Rulkov .............. A61B 5/02438 600/301 |
| 2014/0171759 A1 | 6/2014 | White et al. |
| 2014/0221792 A1 | 8/2014 | Miller et al. |
| 2015/0135310 A1 * | 5/2015 | Lee ................... A61B 5/681 726/20 |
| 2015/0289820 A1 | 10/2015 | Miller et al. |
| 2015/0305675 A1 | 10/2015 | Miller et al. |
| 2015/1313541 | 11/2015 | Rymut |
| 2016/0051191 A1 | 2/2016 | Miller et al. |
| 2016/0120468 A1 * | 5/2016 | Mathew ................. A61B 5/01 600/301 |
| 2016/0235374 A1 | 8/2016 | Miller et al. |
| 2016/0249836 A1 * | 9/2016 | Gulati ................. A61B 5/1455 600/316 |
| 2017/0095233 A1 * | 4/2017 | Heikenfeld ......... A61B 5/0531 |
| 2017/0156594 A1 * | 6/2017 | Stivoric .............. A61B 5/7275 |
| 2017/0303788 A1 | 10/2017 | da Silveira et al. |
| 2017/0071518 A1 | 11/2017 | da Silveira et al. |
| 2017/0319131 A1 * | 11/2017 | Xavier Da Silveira ..................... A61B 5/4875 |
| 2019/0216326 A1 * | 7/2019 | Cross .................... A61B 5/445 |
| 2019/0246976 A1 * | 8/2019 | Howell ................ A61B 5/4875 |
| 2019/0246977 A1 * | 8/2019 | Miller .................. A61B 5/0537 |

OTHER PUBLICATIONS

PCT/US2019/029224 International Search Report and Written Opinion dated Aug. 5, 2019; 8 pages.

Maslakovic, M., "Nobo B60 uses light to measure how much water is in your body", Gadgets & Wearables, Jan. 31, 2019, 3 pages.

Peake, J.M., "A Critical Review of Consumer Wearables, Mobile Applications, and Equipment for Providing Biofeedback, Monitoring Stress, and Sleep in Physically Active Populations", Frontiers in Physiology, Jun. 2018, vol. 9, Article 743, 19 pages.

Jacques, S.L., "Optical properties of biological tissues: a review", Phys. Med. Biol., 2013, 58, R37-R61.

* cited by examiner

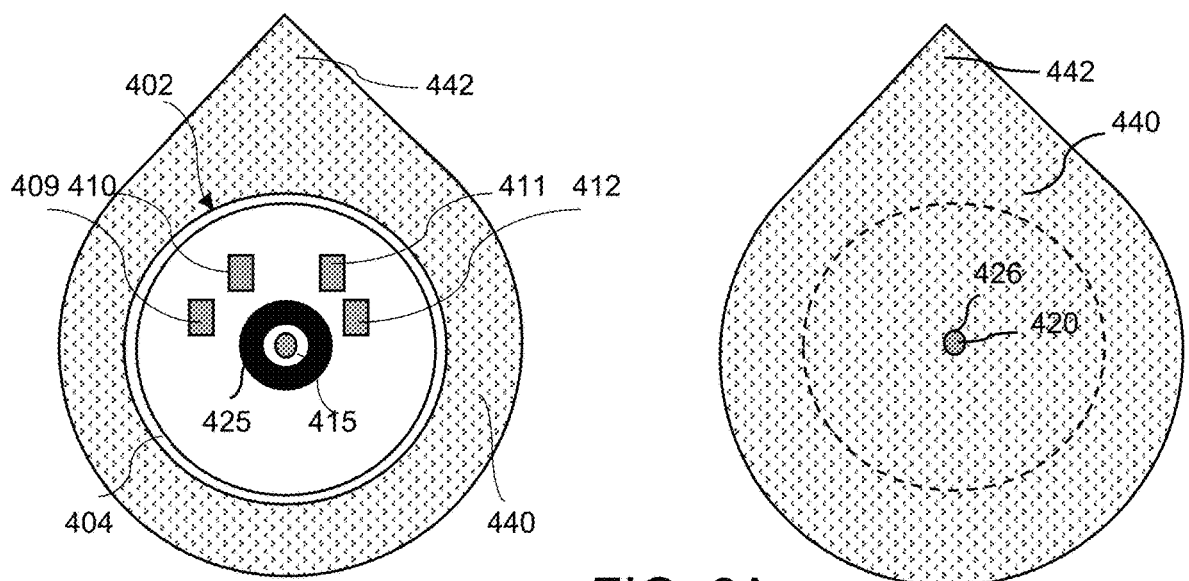
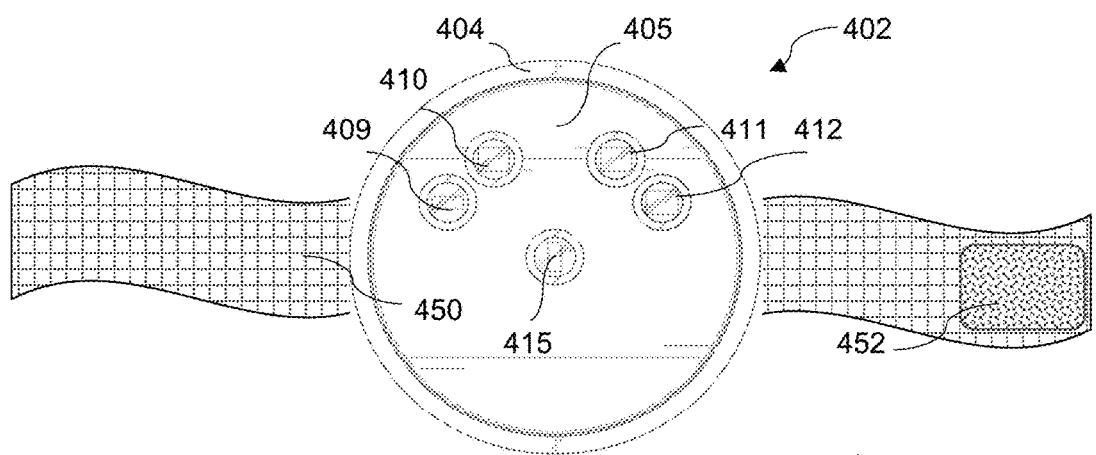
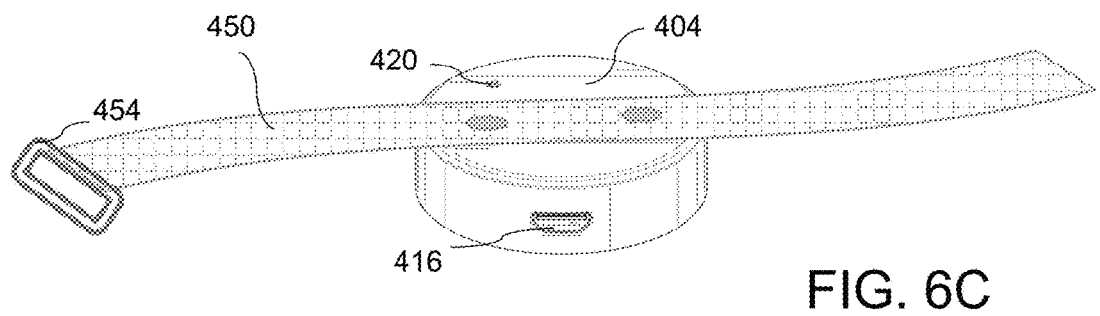
FIG. 6A
FIG. 6B
FIG. 6C

TISSUE HYDRATION MONITOR

RELATED APPLICATIONS

This application claims the benefit of the priority of U.S. Provisional Application No. 62/663,926, filed Apr. 27, 2018, which is incorporated herein by reference in its entirety.

FIELD OF THE INVENTION

The present invention relates to a tissue hydration monitor and more particularly to a tissue hydration monitoring system and method for personalized hydration monitoring.

BACKGROUND OF THE INVENTION

Dehydration is a condition in which water in a living body decreases below the individual's normal functioning level. Dehydration can occur when an individual exerts him or herself for extended periods of time with inadequate water intake to offset losses of internal water from respiration, perspiration, and waste removal, or the temperature rises to a point where an individual cannot produce enough sweat to maintain their normal body temperature. Persons that regularly exert themselves in low humidity and/or high temperature conditions and/or for extended periods of time are prone to experience dehydration or dehydration symptoms. Elderly persons and children are also especially prone to experience dehydration or dehydration symptoms.

In less severe cases of dehydration, an individual's ability to perform tasks may begin to deteriorate. For example, in the case of endurance or professional athletes, an individual that becomes dehydrated by loss of as little as 2% body weight may begin to experience a decline in performance. Low levels of hydration lead to low blood volume, compromising circulation, nutrient exchange, hormone balance, and waste removal. When dehydrated, sodium levels in the blood decrease, resulting in hyponatremia, the first signs of which can include fatigue, headache, weakness and nausea. Additional manifestations include cramping, disorientation and confusion, swelling of extremities, and, in extreme cases, swelling of the brain. Cramping can be common in athletes and is a good key indicator that the body has depleted its electrolytes. Losses in excess of 5% of body weight can decrease the capacity of an individual to perform a task by as much as 30%.

There is currently no wearable sensor on the market that provides accurate and personalized hydration requirements. It is important for athletes to have a self-calibrated measurement of hydration needs because each athlete will have particular needs based on their diet, exercise and genetics. In order to maintain peak performance, it would be desirable to monitor an individual's hydration level regularly, or even continuously, allowing the detection of fluctuations at early stages before performance levels are impacted, and especially before the person approaches a critical dehydration condition. The present invention is directed to a method and device that allows one to easily monitor and provide notification of hydration levels to permit early correction before dehydration occurs.

BRIEF SUMMARY

In an exemplary embodiment, a wearable optical device uses light emitting diodes that emit light and one or more photo diodes that detect light from the skin. In a preferred embodiment, the device will use at least 4 optical wavelengths, e.g., 740 nm, 850 nm, 940 nm, 1450 nm, and a single detector. Other wavelengths may be used, for example, at variations of +/−10 nm based on LED availability and technical adjustments. Ideally, the LEDs and photo diode will be positioned at least 1 cm away from each other with a light blocking partition in between to stop any light from traveling directly from an LED to detector without penetrating the skin. The depth the light will travel in tissue depends on the wavelength and the source-detector separation and tissue constituents, up to several centimeters deep.

The wearable device includes a wireless communication module, for example, BLUETOOTH® or similar wireless communication circuitry and corresponding software, to communicate with a smart phone, tablet, or computer in which an application ("app") has been stored for entering settings and for receiving and storing data.

In one aspect of the invention, the system controller collects information from the user over a pre-determined time period to establish a personalized baseline from which subsequent performance is measured. Thresholds for generating alarms or other indicators of deviation may be pre-set by the system controller, or the user may tighten or expand the threshold range using the associated app. In one embodiment, the system controller, or the associated app on the user's phone, tablet or computer, may execute a learning algorithm or other appropriate algorithm to continuously or periodically update the user's personalized baseline. For example, as the user's conditioning improves, or as the intensity of workouts increases, he or she may experience changes in hydration responses which should be taken into account when determining acceptable ranges.

The device may be fitted with a strap to allow the device to be worn on a wrist, upper or lower arm, ankle, calf, or other location on a limb. The strap should be sufficiently pliable and elastic to firmly press the sensor area against the skin to prevent outside light from entering the sensor, and to ensure that the light-blocking partition is effective in preventing light from the LEDs from being picked up directly by the detector without passing through the skin. In a preferred embodiment, the sensor is temporarily affixed to the skin using a non-irritating, skin-friendly pressure-sensitive adhesive ("PSA"). Such adhesives are commercially available from a number of sources for securing skin-bonded devices for periods of time of a few hours up to a week.

The present invention relies upon on near-infrared spectroscopy of tissues. This method is not novel and has been extensively researched. There have been previous patents filed using the near-infrared spectroscopy method to measure tissue hydration. However, the prior art either uses different wavelengths, different algorithms, or both, and does not provide a personalized calibration system for determining an optimal hydration range.

In one aspect of the invention, a tissue hydration monitor includes a housing configured to be disposed against a user's skin; a sensor module disposed within the housing, the sensor module including: a plurality of LEDs configured to emit light toward the user's skin at a plurality of different wavelengths; and a detector configured to detect light from each of the plurality of LEDs transmitted and reflected through the user's skin over a period of time and generate signals corresponding to an intensity of detected light at each of the different wavelengths; a processor/controller module configured for receiving signals from the sensor module, executing an algorithm for generating a baseline hydration level based on the received signals, calculating a relative hydration level at time points within the period of time, and generating an output indicative of relative hydration at the time points; and a power supply configured to provide power to the sensor module and the processor/controller module. The period of time may include periods of user activity ranging from resting to exercising, wherein the baseline hydration range is generated at time points during resting and the relative hydration level is calculated at multiple time points during exercising. The plurality of different wavelengths are wavelengths absorbed by oxygenated hemoglobin, deoxygenated hemoglobin, lipid, and water and are preferably 740 nm, 850 nm, 940 nm and 1450 nm. An indicator responsive to the processor/controller module is provided for generating an alert indicative of a predetermined deviation from the baseline hydration level. The predetermined deviation is preferably a change of less than or equal to +2%. The indicator may be an LED disposed to emit light from a surface of the housing. A light shield is preferably disposed around the detector to prevent stray light from impinging upon the detector.

In some embodiments, an adhesive material is applied to the housing to removably seal the sensor to the user's skin. The adhesive material may be in the form of a patch dimensioned to seal the perimeter of the housing against the user's skin to produce a substantially light-tight seal. The patch may be formed from at least a breathable material and a water resistant material. In other embodiments, a strap may be attached to the housing for retaining the housing against the user's skin.

The tissue hydration monitor may further include a communication module in communication with the processor/controller module for transmitting data to a remote mobile device for displaying the output. The mobile device may have an application installed therein with instructions for further processing of the output.

In another aspect of the invention, a method for monitoring hydration in a subject includes placing a sensor device against the skin of the subject, the sensor device comprising a plurality of LEDs configured to emit light toward the user's skin at a plurality of different wavelengths; detecting light from each of the plurality of LEDs transmitted and reflected through the user's skin over a period of time and generating intensity signals corresponding to light at each of the different wavelengths; generating a baseline hydration level from the intensity signals; calculating a relative hydration level relative to the baseline hydration level at a plurality of time points within the period of time; and generating an output indicative of relative hydration at the time points. The plurality of different wavelengths are wavelengths absorbed by oxygenated hemoglobin, deoxygenated hemoglobin, lipid, and water and may be 740 nm, 850 nm, 940 nm and 1450 nm. The method may include transmitting data to a remote mobile device for displaying the output and generating an alert indicative of a predetermined deviation from the baseline hydration level, where the predetermined deviation is a change of less than or equal to +2%. The period of time includes periods of subject activity ranging from resting to exercising, wherein the baseline hydration range is generated at time points during resting and the relative hydration level is calculated at multiple time points during exercising.

BRIEF DESCRIPTION OF THE DRAWINGS

FIGS. 6A-6e illustrate different embodiments of the wearable hydration monitor, where FIG. 6A is a diagrammatic view of a sensor (back and front); FIGS. 6B and 6C show the lower and upper sides of a second embodiment of the invention; FIGS. 6D and 6E illustrate alternative LED layouts.

DETAILED DESCRIPTION OF EMBODIMENTS OF THE INVENTION

Figure 1A:
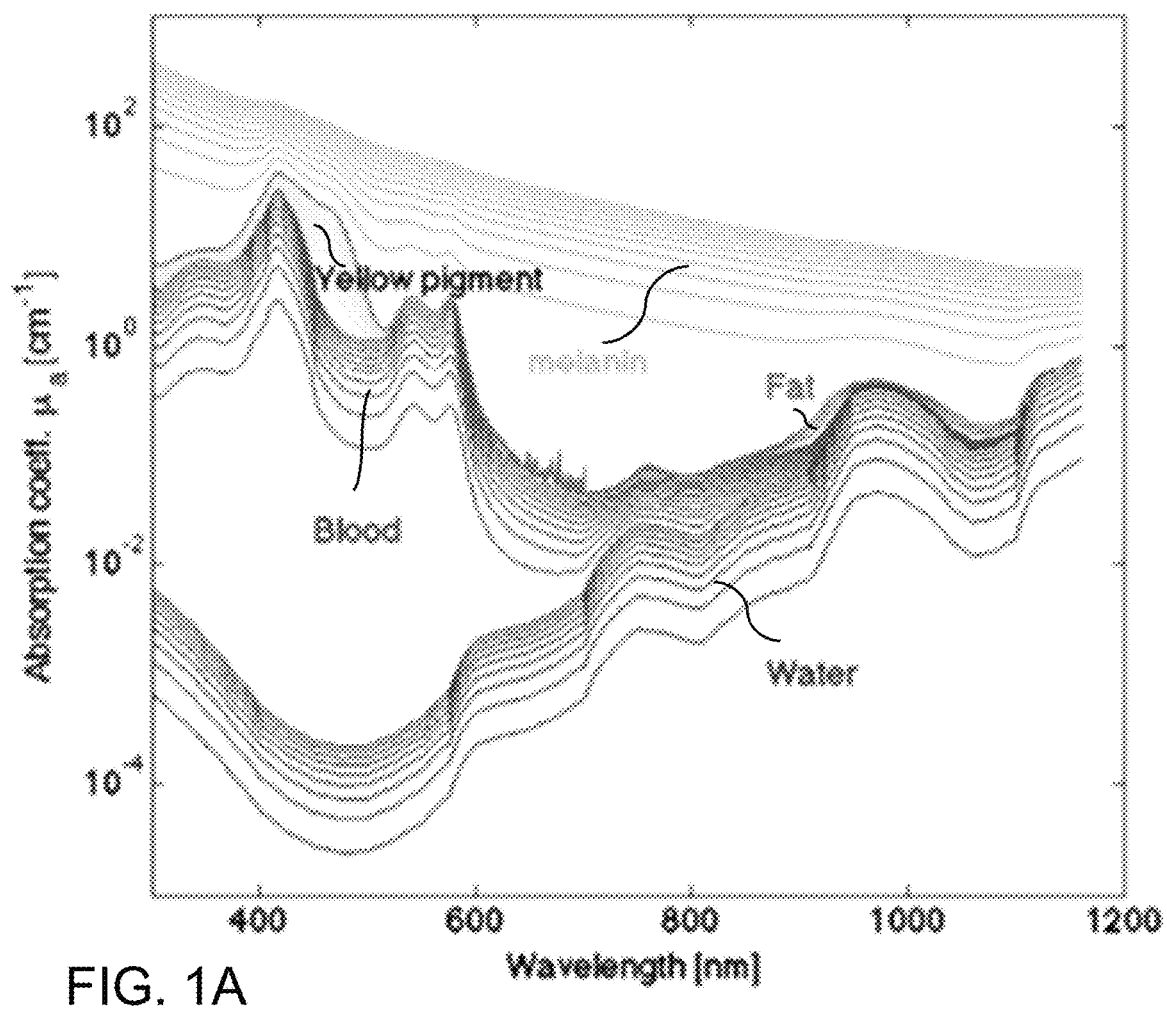
FIG. 1A is a prior art plot showing absorption coefficients of water, whole blood, fat and melanin with several different concentrations of each tissue constituent.
Figure 1B:
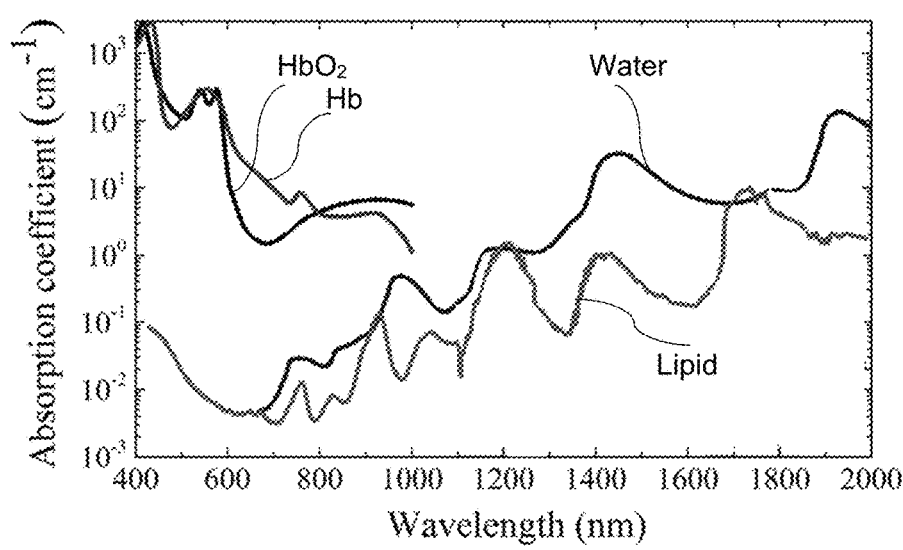
FIG. 1B provides a prior art plot of absorption coefficients of oxygenated hemoglobin, hemoglobin, water and lipid.

Referring to FIG. 1A (from Jacques, infra), absorption coefficients of water, whole blood, fat and melanin with several different concentrations of each tissue constituent are provided for different wavelengths ranging from ultraviolet to infrared. FIG. 1B provides a plot of absorption coefficients of major endogenous agents in biological tissue. Light within the first two wavelength ranges (~740 nm to ~760 nm (red) and ~850 nm to ~940 nm (NIR)) will provide a measure of deoxygenated hemoglobin (Hb) and oxygenated hemoglobin (HbO$_2$) respectively. Using these two measurements, we can determine the tissue oxygen saturation based on known absorption data. See, e.g., S. L. Jacques, "Optical properties of biological tissues: a review," *Phys. Med. Biol.* 58 (2013) R37-R61, Pellicer and Bravo Mdel, "Near-infrared spectroscopy: a methodology-focused review", *Semin Fetal Neonatal Med.* 2011 February; 16(1):42-49. doi: 10.1016/j.siny.2010.05.003, both of which are incorporated herein by reference for purposes of background information on the optical properties of tissues.

A Fourier transform of the 850 nm signal will provide the heart rate of the user. At 940 nm (and again at about 1200 nm and 1420 nm), lipid is the dominant absorptive chromophore, so the signal will provide a measure of lipid content of the tissue. Starting at around 1000 nm, with significant peaks at around 1480 nm and 1950 nm, water becomes the dominant absorber, providing a measure of the water content of the tissue. In the exemplary embodiment, light at 1450 nm (NIR) was selected, primarily for economic reasons, for detecting water absorption Using light with each of the four discrete wavelength ranges together will provide an indication of the scattering and melanin contribution.

Over the time and range scales of interest, the intensity of light received can be approximated by a linear combination of the absorption coefficient $\mu_a$ and the scattering coefficient $\mu_s$.

$$I = A_1 \mu_a + A_2 \mu_s \tag{1}$$

where $A_1$ and $A_2$ are unknown constants that depend on the sensor geometry, electronics, and other factors that will not change appreciably over the time-frames of interest. The absorption coefficient $\mu_a$ has a complicated dependency on wavelength and tissue composition. Over the wavelengths of interest, the scattering coefficient can be approximated to be a linear function of wavelength.

$$\mu_s = s_1 + s_2 \lambda \quad (2)$$

Eq. 3 provides the total absorption coefficient for a generic tissue:

$$\mu_a = BS\mu_{a,oxy} + B(1-S)\mu_{a,deoxy} + W\mu_{a,water} + F\mu_{a,fat} + M\mu_{a,melanosome} + 2.3 C_{bili} \varepsilon_{bili} + 2.3 \beta_C \varepsilon_{\beta C} \quad (3)$$

where S is the HGb oxygen saturation of mixed arterio-venous vasculature, B is the average blood volume fraction ($f_{v,blood}$), W is the water content ($f_{v,water}$), Bili is the bilirubin concentration (C(M)), $\beta$C is the $\beta$-carotene concentration (C(M)), F is the fat content ($f_{v,fat}$), and M is the melanosome volume fraction ($f_{v,melanosome}$), or alternatively, the concentration of melanin monomers (C(M)).

Each term can potentially depend on time and on the wavelength of light. Over the time-frame of interest, the last four terms will not change appreciably over time but on optical wavelength, so they can be lumped into a parameter D. In addition, we are primarily interested in estimating relative changes to hydration (W) from a baseline (starting) value, so $W(t_i)$ is separated into $W_1 + \Delta W(t)$. Writing that out with the explicit dependencies for time wavelength $\lambda$ and time t, $$\mu_a(\lambda, t) = BS(t)\mu_{a,oxy}(\lambda) + B(1-S(t))\mu_{a,deoxy}(\lambda) + (W_1 + \Delta W(t))\mu_{a,water}(\lambda) + D(\lambda) \quad (4)$$

The inventive device will measure the intensity of light at four wavelengths, denoted with $\lambda_k$ and thousands of points in time, denoted with $t_i$.

$$I(\lambda_k, t_i) = A_1(BS(t_i)\mu_{a,oxy}(\lambda_k) + B(1-S(t_i))\mu_{a,deoxy}(\lambda_k) + (W_1 + \Delta W(t_i))\mu_{a,water}(\lambda_k) + D(\lambda_k)) + (s_1 + s_2 \lambda_k) \quad (5)$$

S, the level of HGb oxygen saturation and will vary with each arterial pulse over a time frame of a second or less. Relative hydration $\Delta W$ will change over the time-frame of minutes or hours, and our goal is to track these changes. A variety of signal processing techniques may be applied to estimate $\Delta W(t_i)$ in the presence of the other unknowns $A_1$, $A_2$, $S(t_i)$, $W_1$, D, $s_1$ and $s_2$. One example would be one or more least-squares fits (regression) using all of the $I(\lambda_k, t_i)$ data recorded by the device over the period of minutes or hours. Temporal band-pass filtering of $I(\lambda_k, t_i)$ may be employed, if appropriate, to separate spectral components of I.

Relative hydration values may be used to generate the user's personal hydration index ("PHI"). In an exemplary implementation, for the initial set of measurements (i.e., the "training data"), the first 3 min of a training session is used to establish an average intensity value for the sensors' four LEDs. Data is then collected for the duration of the training session. At the end of the training session, the average intensity value for the entire session is taken as the baseline for the next session. Notifications indicating "out of optimal range" can be initially pre-set at a threshold of 2% from baseline based on general agreement within the scientific literature that this deviation corresponds to onset of cognitive defects. In a preferred embodiment, notifications would be generated before a change of +/-2% occurs to allow sufficient time for the user to rehydrate before an out of range condition is reached. During a given training or activity session, i.e., a monitored time period, the inventive device will periodically measure and calculate relative hydration to determine the user's relative hydration level at a number of time points, where the monitored period of time may include periods of activity ranging from resting to exercising. The type of exercise with vary with the individual, and may range from walking to intense athletic activity. At any given time point during the monitored time period, the inventive device may generate a notification if the measured relative hydration approaches or exceeds the predetermined threshold to prompt the user to rehydrate. Notifications may occur at multiple time points during exercising, particularly in extended periods of intense activity.

Ideally, notifications will be generated prior to the point at which the user's performance could be impacted by hydration status. In testing of the prototype, a sensitivity of 0.1% was achieved, which is 10× more sensitive than thirst (1-2%). With more data and more advanced analytics, the range may be personalized to allow the user to set his or her own ideal threshold to allow proactive hydration to maintain the user's optimal hydration level throughout an activity. In other embodiments, signal processing techniques such as machine learning and data mining may be employed to derive a relationship between $I(\lambda_k, t_i)$ and $\Delta W(t_i)$ to generate the user's PHI and appropriate notification thresholds.

Figure 2:
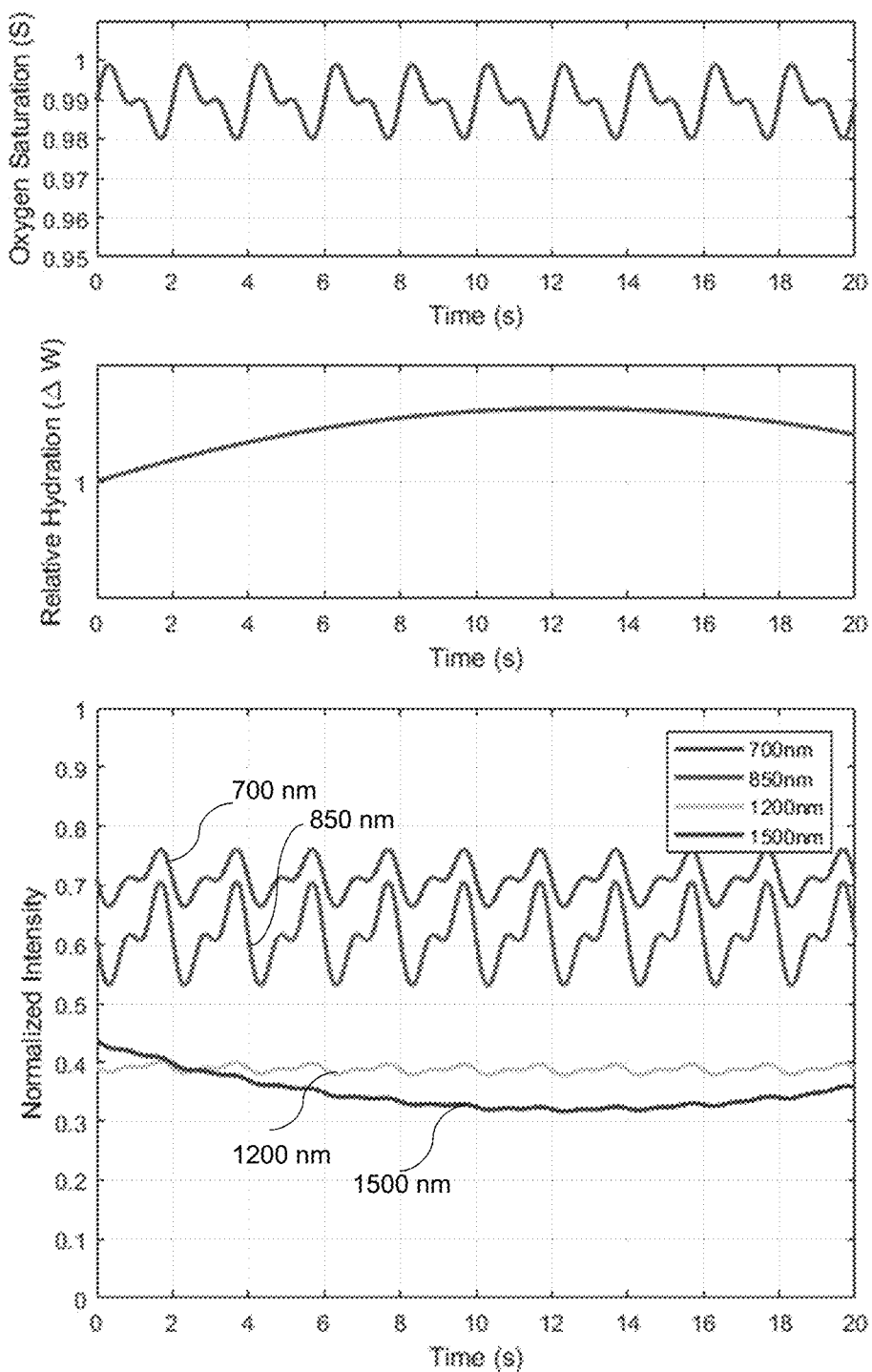
FIG. 2 plots how oxygen saturation S and relative hydration level $\Delta W$ may change over time and how they will appear in the received optical intensity.

FIG. 2 illustrates how oxygen saturation S (upper panel) and relative hydration level $\Delta W$ (center panel) may change over time, and how they will appear in the received optical intensity (lower panel) for example wavelengths of 700 nm (for $HbO_2$), 850 nm (for Hb), 1200 nm (for lipid), and 1500 nm (for water).

Figure 3A:
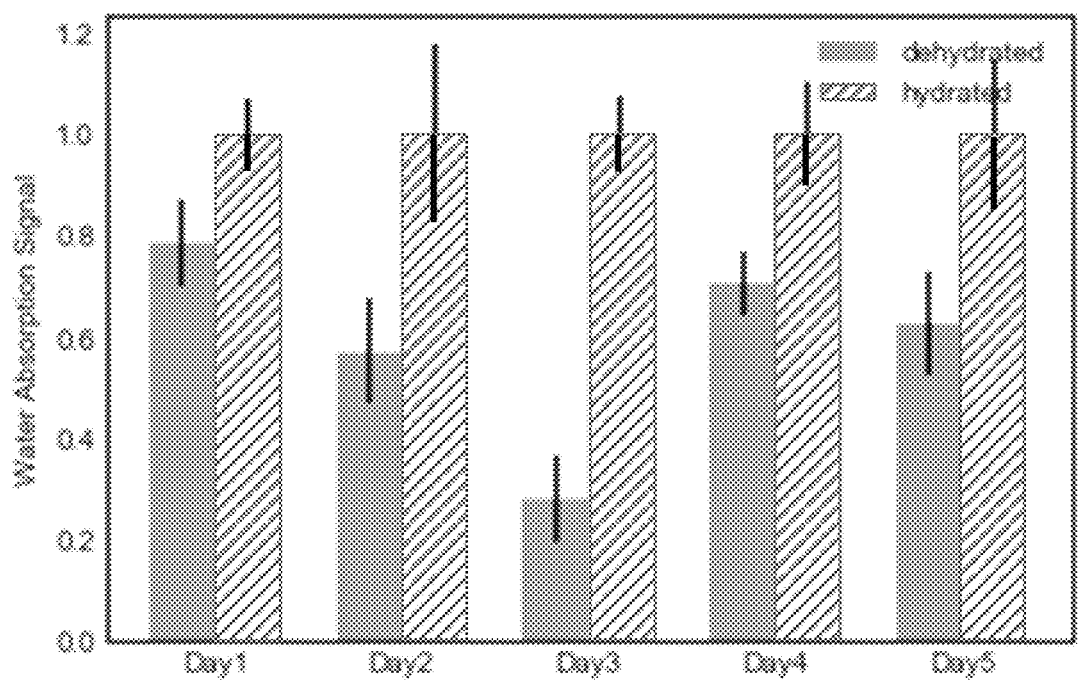
FIG. 3A is a graph showing hydration versus dehydration measured over a five day period using water absorption in accordance with the inventive approach.
Figure 3B:
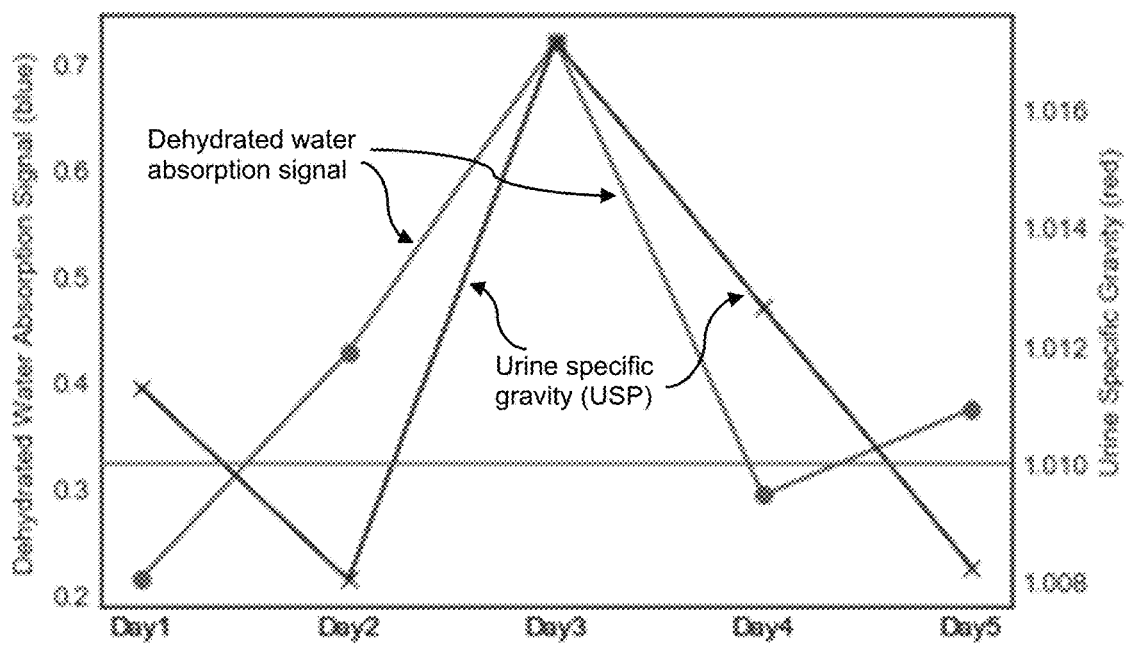
FIG. 3B is a plot comparing dehydration measurements obtained using water absorption and urine specific gravity over the same period.

FIGS. 3A and 3B are plots of water absorption measurements taken over a period of five consecutive days. FIG. 3A shows the normalized water absorption levels for the test subject for each day upon waking (dehydration) and one hour after drinking 473 ml (16 ounces) of water (hydration). During the one hour period, the subject engaged in light activity and ate breakfast. In each case, the measurement duration was 5 minutes. The detected values were averaged over the collection period then normalized, with hydration being used for normalization. FIG. 3B compares the results of dehydration water absorption measurements using a 1450 nm signal to urine specific gravity (USP) measurements for urine collected upon waking (dehydration), showing good correlation. The line at 1.01 USP is the delineation where any measures above 1.01 USP is considered dehydrated.

Figure 4:
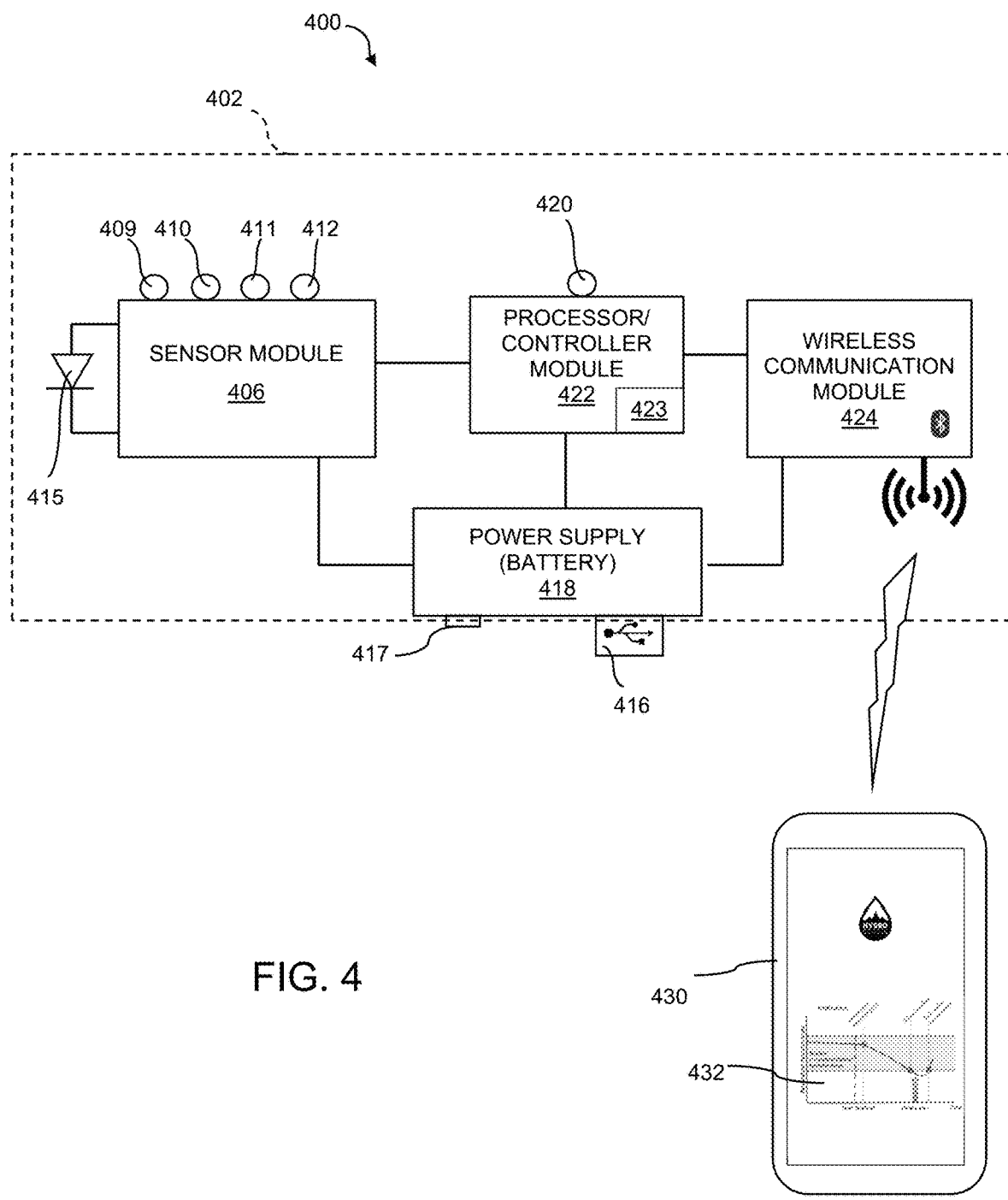
FIG. 4 is a block diagram of the basic components of an embodiment of the inventive hydration sensor.

Referring first to the hydration monitoring system 400 diagram in FIG. 4, within the sensor assembly 402 are three main modules: the sensor module 406, the processor/controller module 422, and the wireless communication module 424. In sensor module 406, the LEDs 409-412, i.e., LED1, LED2, LED3, and LED4, can be controlled to pulse on and off sequentially, while the detector 415 detects continuously to measure the intensity of reflected light from each of the LEDs. Power for components within the sensor assembly 402 is provided via a battery 418, preferably rechargeable through a USB or similar charging port 416. In some embodiments, inductive charging circuitry, such as is widely used in smart watches and some smart phones, may be included. On/off switch 417 may be provided to enable manual control of power consumption. The data that is collected will be processed through the processor/controller module 422, the results of which may be stored in memory 423 then transmitted via a BLUETOOTH® (or similar wireless communication module 424) to a mobile application 432 downloaded onto a smart phone 430, tablet, computer, or other personal portable device. The user will be able to interact with the device using the mobile application 432 ("app") and determine his or her current hydration status as well as review past measurements. Indicator light (LED) 420 is connected to processor/controller module 422 to provide quick visual feedback to alert the user when preset conditions, e.g., dehydration or overhydration, are detected. Alternatively, or in addition to the indicator light 420, the sensor device may include an audio or vibration device connected to the processor/controller module 422 for generating an audible or haptic alert to indicate that the user's hydration level is no longer within the desired optimal hydration range.

Figure 5:
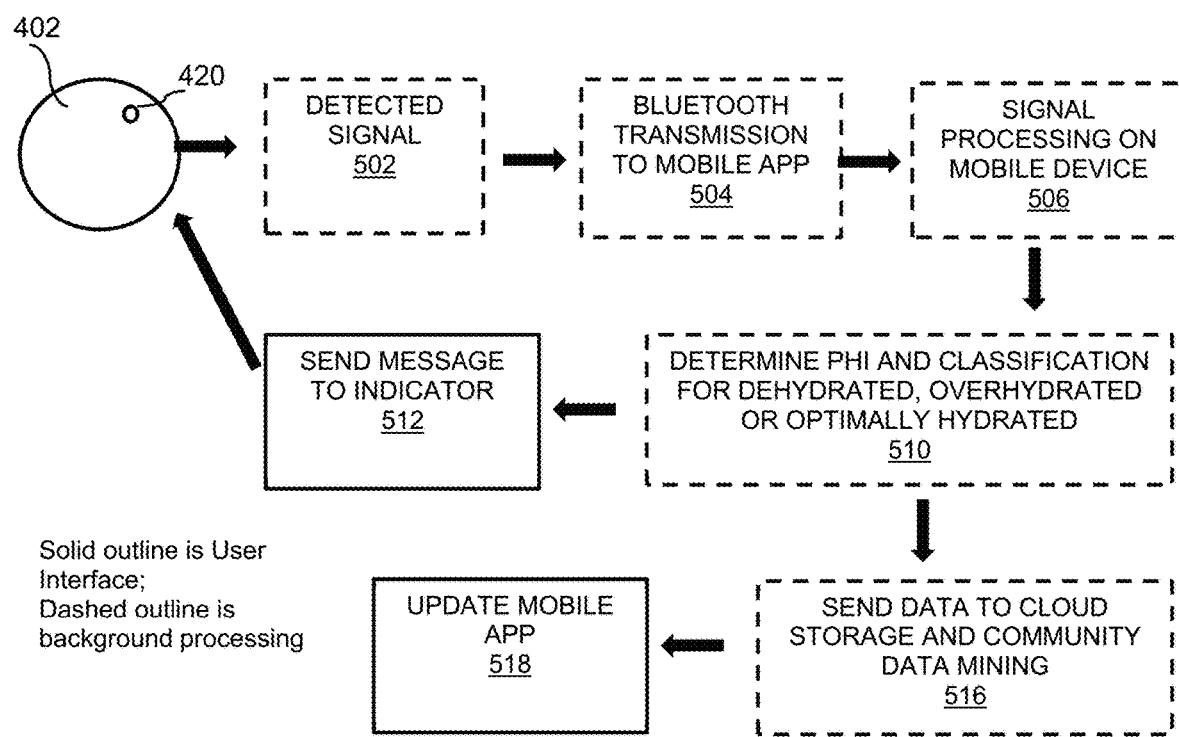
FIG. 5 is a block diagram showing data processing flow according to an embodiment of the inventive sensor system in which the user interface components and background processing components are indicated.
Figure 7:
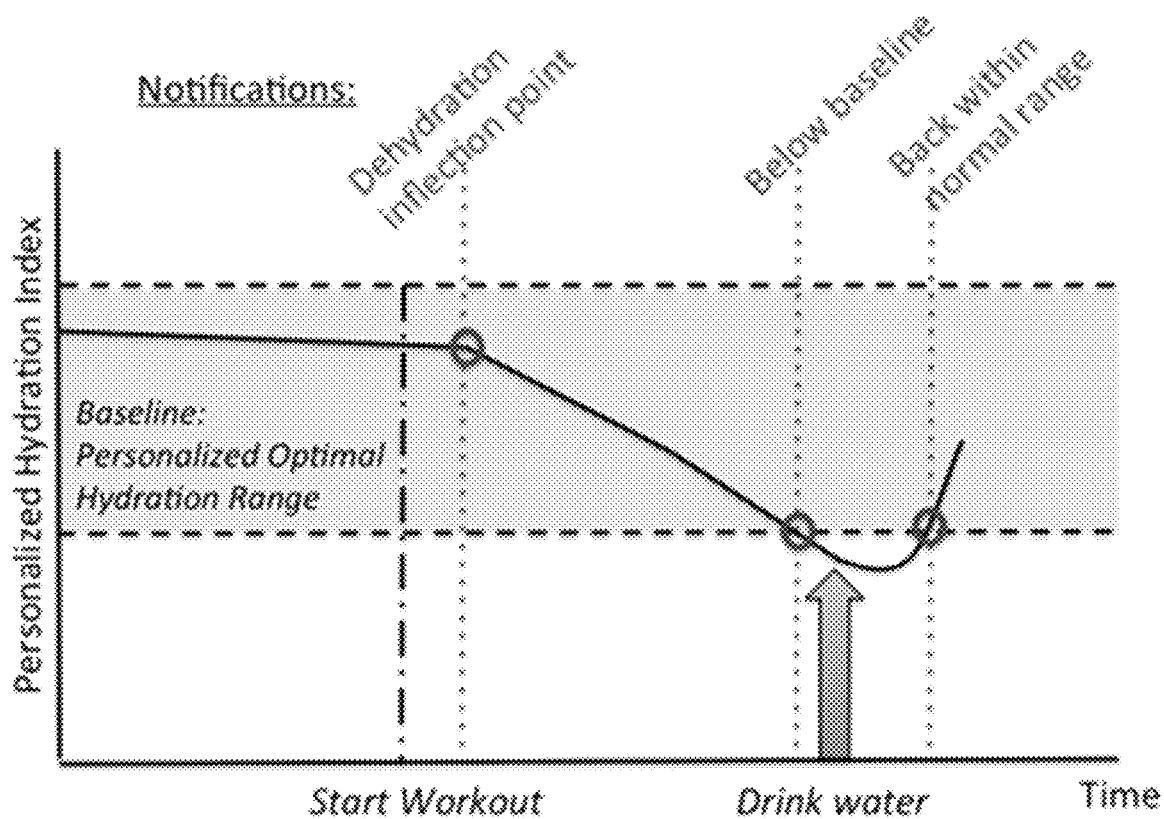
FIG. 7 is a plot of exemplary hydration data with time for a personalized hydration index.

FIG. 5 provides a flow diagram of functions within various components of the inventive monitoring system. In the diagram, elements with a solid outline indicate user interface while the dashed outlines indicate background processing. Sensor assembly 402 is activated after being placed in close contact with the user's skin. The LEDs are activated and an optical signal is detected and processed within processor/controller module 422. The detected signal 502 is transmitted via wireless transmission 504 to the mobile device 430, which has been previously loaded with the mobile app 432. In step 506, the app 432 executes processing within the mobile device 430, including establishing a baseline range for the user's personal hydration index ("PHI") based on relative hydration and normalized intensity using the algorithms described above, then comparing the corresponding values of the currently detected signal to the PHI to determine whether the user is dehydrated, overhydrated or within this or her range of optimal hydration (step 510). Referring briefly to FIG. 7, a sample plot of exemplary hydration data with time for a personalized hydration index (PHI) determined through an initial calibration period is shown. In the plot, the y-axis is the PHI with the baseline optimal hydration range indicated in the shaded region, with activities indicated along the x-axis that initiate changes in the user's hydration level relative to the optimal range.

Returning to FIG. 5, in one embodiment, in step 512, a determination that the user is within the optimal range may result in a message being sent to sensor assembly 402 to activate a green display at indicator light 420, while being out of range could generate a red or yellow display. In another embodiment, step 512 could active different colors for each of under-, over-, and optimal hydrations, for example, a blue light for overhydration, red for underhydration and green for optimal. A yellow display could provide an additional indication that the user is approaching the limits of their optimal range. As noted above, step 512 may alternatively or in addition cause an audible or haptic alert to be generated. In step 516, the determined hydration level can be sent to a remote data collection/storage medium for use in, e.g., community data mining. To provide one example of possible applications of this step, the data could be collected by a coach or team trainer who may be on the sidelines monitoring athletic performance of a number of team members, providing additional data for decisions on player substitution or for developing insights into impacts of hydration on the team's performance. In step 518, the mobile app can be updated to include the current data to allow a history to be stored.

The device incorporates both novel hardware and software. As shown in FIGS. 6A-6E, in an exemplary embodiment, the housing 404 of the wearable sensor 402 is a flattened disk, typically having a diameter on the order of 25-60 mm (~1-2.5 in.) and a thickness of about 8-12 mm (~0.3-0.5 in.). The dimensions may be revised as technological advances permit further miniaturization of the sensor components. While the shape of the housing 402 is shown as generally circular in cross-section, it will be readily apparent that additional shapes may be used. For example, an ellipsoidal shape could be used as well as polygons that have sufficiently large corner angles to avoid sharp corners that could cause skin irritation or injury should the device be impacted during athletic activity. Further, although the profile of the housing 404 is illustrated as generally flat with a uniform thickness across the full diameter, the perimeter of the housing may be tapered toward the edges to create a plano-convex profile. The edges of the housing should be beveled or rounded to reduce edges that could cause injury to anyone coming into contact with the device during athletic activity. A silicone-based (non-irritating, non-allergenic) adhesive may be used to enclose and seal the housing to protect the device electronics against moisture intrusion from perspiration and other liquid exposure. As discuss above with reference to FIG. 4, the hardware encased within the housing includes the battery 418, LEDs 409-412, 420, photodiode (optical detector) 415, mini-USB port 416, switch 417, voltage regulators, microcontroller, analog front-end (all in processor/controller module 422) and BLUETOOTH® or similar wireless communication module 424.

The battery 418 and BLUETOOTH® 424 will allow the device to operate and communicate wirelessly with the mobile application 432. The mini-USB port 416 will allow charging of the battery as well as wired data transfer. The voltage regulators, microcontroller, analog front-end will power and control the sensor. The battery life must be sufficient to drive the LEDs, data collection, indicator lights, and Bluetooth data transmission for at least 24 hrs.

FIG. 6A illustrates an embodiment of the wearable sensor that utilizes an adhesive fabric patch 440 to removably affix the sensor 402 to the user's skin to ensure close and continuous contact for extended periods and/or during activity. A silicone-based adhesive system will keep the device in place and provide water resistance. Skin-friendly adhesives are commercially available for attachment of sensors and similar devices for periods ranging from a few hours to about a week. The adhesive should be able to stay on the skin and measure comfortably for at least 24 hrs. In some embodiments, the adhesive may be a liquid or gel that can be applied directly to the skin using an applicator or brush. The patch should be sufficiently flexible, e.g., a foam, gel, fabric, or combination thereof, to avoid skin irritation. The adhesive fabric patch 440 has a larger diameter than the sensor housing so that the entire perimeter of the patch contacts and adheres to the user's skin to provide a light-tight and water-resistant seal around the sensor. A small opening 426 in the patch 440 allows the indicator light 420 to be viewed. The patch may be, for example, a thin Neoprene® material with a non-irritating adhesive, pre-cut to the correct dimensions to achieve the desired coverage, or kinesiology tape, e.g., KT Tape®, may be cut to size to hold the sensor in place. Extension tab 442 in the pre-cut patch provides an easily-grasped feature to facilitate application and removal of the patch.

Figure 8:
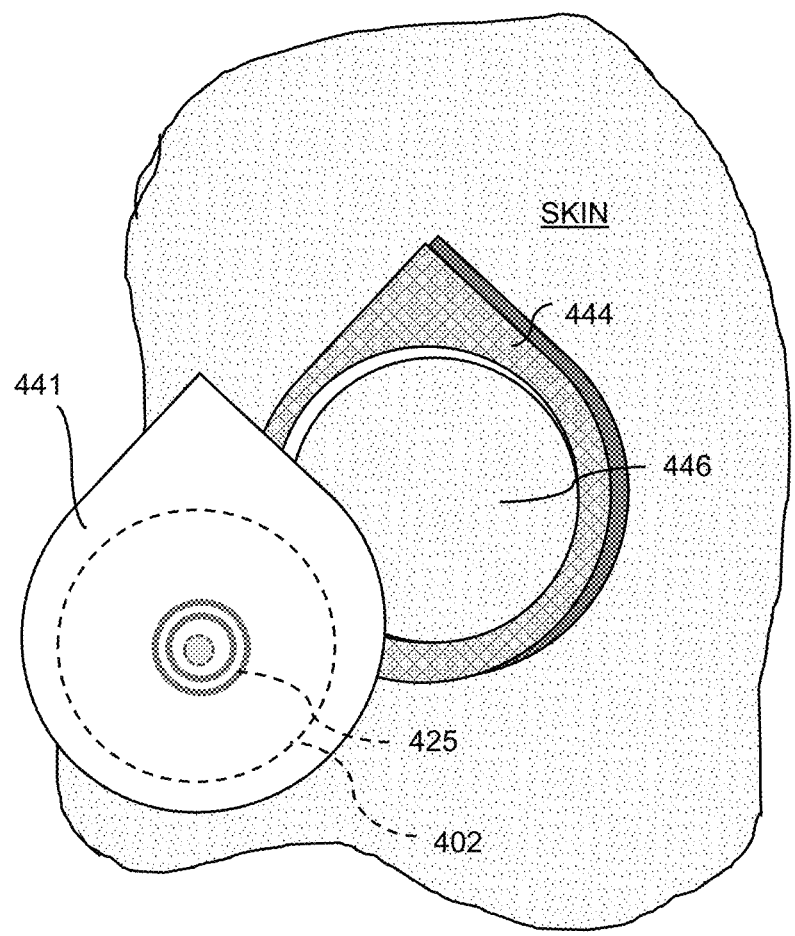
FIG. 8 is an exploded view demonstrating attachment of an embodiment of the inventive device to the user's skin.

FIG. 8 illustrates an example of application of the sensor to a user's skin using a pre-cut multi-ply adhesive patch, which includes a double adhesive middle layer 444 that is cut to match the outer shape of patch 441, which is in contact with the outer surface of sensor 402. In some embodiments, the outer patch 441 may be permanently attached to the outer surface of the sensor housing 404, with only the middle layer 444 being replaced, while in other embodiments, outer patch 441 may be removable and replaceable, provided as a package with the middle layer 444, with removable backing sheets that can be peeled off to expose fresh adhesive for application to the skin. The center opening 446 in middle layer 444 fits closely around the edges of sensor 402 to provide a light-tight seal around the device to prevent exterior light from being picked up by the detector 415. The middle layer 444 (facing the skin), may be formed from a water absorptive material to absorb perspiration from exercise, minimizing the contribution of signal artifacts due to moisture. The outside facing layer 441 of the adhesive system is preferably breathable for airflow, to prevent overheating as well as allowing skin to stay dry. The design of the adhesive patch is important to the performance of the sensor in terms of moisture and light control. In general, the patch, whether single ply or multi-ply should be able to hold the sensor in place for 24 hrs and limit movement between the skin and the device, while allowing the skin to remain sufficiently dry to minimize signal artifacts from perspiration.

In the exemplary implementation, light sources 409-412 are LEDs selected to emit light at each of 740 nm, 850 nm, 940 nm, and 1450 nm, for detecting absorption by oxygenated hemoglobin ($HbO_2$), deoxygenated hemoglobin (Hb), lipids, and water, respectively. The specific combination of wavelengths selected are unique in that they collectively provide a comprehensive personalization of the measurements including fat content, skin color, tissue oxygenation, heart rate, and water content. It should be noted that the detection targets exhibit absorption peaks at other wavelengths, and that selection of appropriate combination of LEDS and wavelengths will be within the level of skill in the art. In general, any combination of wavelengths in the range of 600-2000 nm that is sufficient to provide blood flow, oxygen saturation, lipid and water content may be used. In one embodiment, the LED wavelengths can be changed to target the spectra of other or additional chromophores of interest. Different algorithms to normalize and process the data can also be applied to achieve similar/improved results. Various classification algorithms may be used to achieve similar/improved results as well.

Referring to FIG. 6A, LEDs 409-412 are positioned within the plane of the contact surface 405 of the sensor to at least partially surround, and be equidistant from, detector 415. Light guard ring 425 encircles detector 415 to prevent light from the LEDs from directly entering the detector from the sides, so that only light reflected up through the skin impinges on the detector 415. Since guard ring 425 is preferably pressed firmly against the user's skin to create a good seal against light intrusion, it should be formed from a soft, pliable material such as silicone O-ring or a similar compressible, non-irritating material.

The housing 404 will preferably be formed of an opaque (non-light-transmissive) plastic or polymer material, e.g., black or dark colored, to minimize stray light being reflected or transmitted. The housing may be formed of two halves, closely fitted together and sealed to minimize moisture intrusion into the interior of the device. In some embodiments, the housing 404 may be a rigid material, a rigid material with an elastomeric coating (for comfort and/or increased safety), or an elastomeric material with sufficient rigidity to provide protection for the electronic components enclosed therein. It may be desirable to fill the interior of the housing with a potting material or other protectant to ensure that the electronic components are well protected against moisture and impact. Each of LEDs 409-412, indicator light 420, and detector 415 will preferably be located behind transparent windows that are sealed to the interior of the housing to create a waterproof seal. The windows may be partially recessed within the surface, i.e., not flush with the contact surface 405, to serve as a light shield to minimize lateral light leakage into the detector.

The embodiments of FIGS. 6A and 8, with the adhesive patch fastener, provide an advantage that the sensor may be affixed anywhere on the user's body where there is a sufficiently flat surface area to achieve a good seal. FIGS. 6B and 6C illustrate an alternative approach to affixing the hydration sensor to the user's skin that would generally be applied to a limb or area of the body where a belt or strap can be worn. In this embodiment, the sensor housing 404 is attached to a strap 450 that can be wrapped around a user's arm or leg. As shown in FIG. 6B, the strap 450 can be attached using a hook-and-pile type fastener, e.g., VELCRO®, while in FIG. 6C, the strap is shown including a buckle 454 attached to the strap. In either variation, the strap 450 will preferably be sufficiently elastic to firmly but comfortably hold the sensor against the user's skin with minimal slippage.

Figure 6D:
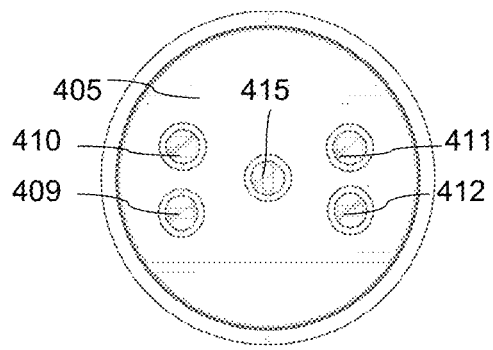
Figure 6E:
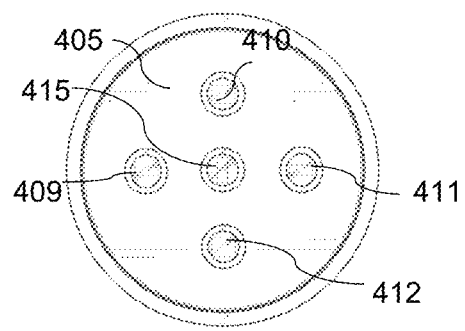

FIGS. 6D and 6E illustrate alternative arrangements of the LEDs and detector. In each case, the LEDs are positioned to at least partially encircle the detector 415, which is generally located near the center of the skin contacting surface 405 of the housing 404. The positioning of the LEDs relative to the detector is designed to aid in identification of motion artifacts through signal processing methods. Other arrangements following the same general configuration will be readily apparent to those of skill in the art.

The data processing algorithms described above are used to generate the personal hydration index (PHI), which takes into account light scattering, melanin, lipid content, and blood flow as well as water content. Another parameter that may be measured and incorporated into the algorithms is heart rate. The algorithm may use the heart rate frequency of the water content to measure the arterial water content. When water is consumed, it is first absorbed into the blood stream from the stomach before being distributed to skeletal muscle. The lipid content can be used to normalize the PHI to athletes having a different Body Mass Index (BMI). Testing may be required to determine a maximum BMI at which the device may not be effective in providing an accurate measurement due to a thicker lipid layer. The algorithm to use the heart rate to isolate and ensure the water measurement is coming from arterial blood is novel. The algorithm to normalize the data using individualized scattering coefficients as well as lipid content is novel. The algorithm to combine all the measurements into a personalized hydration index is novel.

For use, the user will preferably place the device on an area of skin that directly overlies a major artery and which has a sufficiently flat and smooth area, e.g., free of folds, bends, wrinkles, or protruding scars, to allow the sensor to lay flat on the skin. Possible locations include the brachial artery on the inside of the bicep, the posterior tibial artery behind the calf, and femoral artery on the inside of the thigh. As previously described with reference to FIGS. 6A, 6B and 8, the device may be applied using a s double-sided adhesive patch that can be left on the body for at least 24 hrs. After washing the area, the user may then re-apply the device by replacing the adhesive patch to continue monitoring their PHI.

Motion artifacts can be a major issue for light detection on the skin. Approaches to minimize these motion artifacts include ensuring the adhesive is applied to keep the sensor on the skin without separation. Use of a water absorbing material on the adhesive patch will help absorb sweat accumulated during exercise. For embodiments employing an adhesive patch, the patch should be formed of a breathable material to allow airflow and minimize moisture accumulation between the sensor and the skin. LED pulse frequencies may be set up as semi-random to avoid repeated frequencies that may contribute to motion artifacts, such as the heart rate. By using a moving average of the data points, it is possible to smooth out the data and exclude large artifacts due to exercise movement.

The calibration period for establishing the personal baseline should preferably be at least 12 hrs, during which the high and low limits of the PHI are calculated. The calibration procedure should preferably be performed on a day of relatively low movement by the user to allow for more accurate determination of the optimal hydration range. The LEDs can also be turned on and off at different frequencies to avoid heart rate synchronizing with any movement artifacts (heartbeat).

Another approach to establishing the baseline PHI can include employing a hybrid procedure: a long collection time (12 hrs), or using a pre-determined "standard PHI", then continuously updating the baseline with each successive workout to gradually personalize it for the user. Using the PHI, relative changes in hydration during periods of exercise can be determined.

In some embodiments, for example, where the hydration monitors are used on team athletes, the data can be collected for monitoring by a coach or trainer, with identifying information intact, to allow the coach or trainer to identify individual players who may need to be called in from the activity to rehydrate. In other embodiments, the data can be stripped of identifying information and stored in a cloud for data mining purposes. Each user may be labeled using one or more tags that classify the user's athletic grouping. For example, labels may include, but not be limited to, exercise of choice, resting heart rate, height, weight, gender, ethnicity, exercise duration, exercise intensity, athletic classification, e.g., amateur or professional, or other characteristics that can be used to distinguish among factors that may impact hydration and/or sensitivity to fluctuations in hydration.

Using these labels, various data mining algorithms may be used to classify the athlete as over-hydrated, dehydrated, or optimally hydrated based on their PHI. Possible data mining algorithms include learning machines (neural networks, support vector machines, Bayesian networks, genetic algorithms, etc.), statistics, clustering, regression, etc. The computational processing may either be done locally on the mobile application, or on a cloud computing system, in which measurements may be compared against populations of persons falling within the same or similar classifications based on data accumulated from other users and stored in a central database. Data analytics may include feature selection and machine learning algorithms to identify attributes that are most determinative of hydration. Once the classification(s) is/are made, one or more indicator LEDs may be activated to display, for example, red for measurements out of optimal range, green for inside optimal range, and yellow or orange for insufficient data/error or for nearing out of optimal range. The user can access more detailed information through the mobile application.

The more data that is collected, the more accurate the PHI will be, and classification algorithms will become more robust to indicate dehydration, over hydration, or optimal hydration. Measurements can be improved by applying more than one sensor on the body. By measuring in different areas of the body, it is possible to generate an overall total body average of hydration, rather than a point measurement. This technique may be useful in discarding outlier data due to artifacts at one location.

The use of more than one sensor will necessitate more than one adhesive patch (or strap) and an modified data processing algorithm to combine the measurements and tease out the artifacts. A combined total body personal hydration index (PHI) can be calculated from the multiple measurement sites.

In some situations, the user may not want to make continuous, real-time measurements during activity. In these situations, an adhesive or strap need not be applied. Instead, the user can simply place the sensor on dry skin for measurement periods, such as before and after a workout, to provide two measurement points. Assuming the calibration of the optimal hydration range has already been achieved, this simple measurement with provide data indicating how much water loss occurred during a given exercise session. A similar approach may be used if the user wishes to monitor his or her hydration during time outs or other interruptions in activity. To provide a practical illustration, it is not uncommon for athletes to suffer severe muscle cramping during football games or tennis matches. A quick measurement during a break in play could allow the athlete to quickly determine whether they are approaching dehydration and take preventive measures, before actual cramping occurs.

The software includes a self-calibration algorithm, using the high and low hydration range in at least one calibration day (24 hrs) before the device is ready to accurately determine a personalized optimal range, taking into account, tissue scattering, lipid content as well as water content. Once the optimal range is determined, the device will be able to determine percentage PHI changes, indicating over-hydration, dehydration, or optimal hydration during exercise. The more measurements the user logs, the more accurate the optimal range becomes and therefore the more accurate PHI predictions.

The user may decide to use only this or her own measurements, in which the processing can be processed in the mobile application, or he or she may choose to access data from other users on the cloud using cloud computing techniques as are known in the art. Ideally, once enough data is loaded onto the cloud, the athlete will be able to compare and contrast his/her athletic level and hydration needs against other athletes of similar categories.

Novel aspects of the inventive device and method include the specific preprocessing of the data to feed into classification algorithms as well as the option to either run the classification locally on the mobile application or using cloud computing.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

The invention claimed is:

1. A tissue hydration monitor, comprising:
a housing having a planar contact surface with a contact surface area configured to be secured substantially flat against an area of skin of a user's limb;
a sensor module disposed within the housing, the sensor module comprising:
a detector disposed within the contact surface area; and
four LEDs arranged within the contact surface area to at least partially encircle the detector, the four LEDs configured to sequentially emit pulses of light from the contact surface toward the area of skin, each of the four LED emitting at a different wavelength corresponding to one of a plurality of chromophores of interest;
wherein the detector is configured to sequentially detect light from each of the four LEDs that is transmitted and reflected through the area of skin over a period of time and to generate signals corresponding to an intensity of detected light at each different wavelength;
a processor/controller module configured for receiving signals from the sensor module, executing an algorithm for generating a baseline hydration level based on the received signals, calculating a relative hydration level at time points within the period of time, and generating an output indicative of relative hydration at the time points; and a power supply configured to provide power to the sensor module and the processor/controller module.

2. The tissue hydration monitor of claim 1, wherein the housing is secured against the area of skin by a double-sided adhesive material applied to the housing and to the skin.

3. The tissue hydration monitor of claim 1, wherein the housing is secured against the area of skin by a removable strap attached to the housing.

4. The tissue hydration monitor of claim 1, wherein the chromophores of interest are oxygenated hemoglobin, deoxygenated hemoglobin, lipid, and water.

5. The tissue hydration monitor of claim 1, wherein the different wavelengths comprise a first discrete wavelength in the range of 740 nm to 760 nm, a second discrete wavelength in the range of 850 nm to 940 nm, a third discrete wavelength selected from 940 nm, 1200 nm, and 1420 nm, and a fourth discrete wavelength selected from 1000 nm, 1450 nm, 1480 nm and 1950 nm.

6. The tissue hydration monitor of claim 1, further comprising a communication module in communication with the processor/controller module for transmitting data to a remote mobile device for displaying the output.

7. The tissue hydration monitor of claim 6, wherein the mobile device has an application installed therein comprising instructions for further processing of the output.

8. The tissue hydration monitor of claim 1, further comprising an indicator responsive to the processor/controller module for generating an alert indicative of a predetermined deviation from the baseline hydration level.

9. The tissue hydration monitor of claim 8, wherein the indicator comprises an LED disposed to emit light from a surface of the housing.

10. The tissue hydration monitor of claim 8, wherein the predetermined deviation is a change of less than or equal to ±2%.

11. The tissue hydration monitor of claim 1, further comprising a light shield disposed around the detector to prevent lateral light leakage from the four LEDs from impinging upon the detector.

12. The tissue hydration monitor of claim 1, wherein the period of time includes periods of user activity ranging from resting to exercising, wherein the baseline hydration range is generated at time points during resting and the relative hydration level is calculated at multiple time points during exercising.

13. A method for monitoring hydration in a subject, the method comprising:
securing a sensor device substantially flat against an area of skin of the subject's limb, the sensor device comprising a detector and four LEDs disposed in a housing having a planar contact surface, the four LEDs arranged within the planar contact surface to at least partially encircle the detector, each of the four LEDs configured to sequentially emit pulses of light toward the area of skin at different wavelengths each corresponding to one of a plurality of chromophores of interest;
sequentially detecting light from each of the four LEDs transmitted and reflected through the area of skin over a period of time and generating intensity signals corresponding to light at each of the different wavelengths;
generating a baseline hydration level from the intensity signals;
calculating a relative hydration level relative to the baseline hydration level at a plurality of time points within the period of time; and
generating an output indicative of relative hydration at the time points.

14. The method of claim 13, wherein the chromophores of interest are oxygenated hemoglobin, deoxygenated hemoglobin, lipid, and water.

15. The method of claim 13, wherein the different wavelengths comprise a first discrete wavelength in the range of 740 nm to 760 nm, a second discrete wavelength in the range of 850 nm to 940 nm, a third discrete wavelength selected from 940 nm, 1200 nm, and 1420 nm, and a fourth discrete wavelength selected from 1000 nm, 1450 nm, 1480 nm and 1950 nm.

16. The method of claim 13, further comprising transmitting data to a remote mobile device for displaying the output.

17. The method of claim 13, further comprising generating an alert indicative of a predetermined deviation from the baseline hydration level.

18. The method of claim 17, wherein the predetermined deviation is a change of less than or equal to ±2%.

19. The method of claim 13, wherein the period of time includes periods of subject activity ranging from resting to exercising, wherein the baseline hydration range is generated at time points during resting and the relative hydration level is calculated at multiple time points during exercising.

20. The method of claim 13, further comprising generating a personal hydration index (PHI) by:
calculating average hydrated intensity values for the four LEDs over an initial calibration period after subject hydration;
collecting intensity values over a full calibration period;
normalizing the collected intensity values using the average hydrated intensity values;
calculating average normalized collected intensity values to establish a baseline PHI.

21. The method of claim 20, wherein the PHI is updated with each successive activity period.

* * * * *